(12) United States Patent
Kipman et al.

(10) Patent No.: US 6,778,714 B1
(45) Date of Patent: Aug. 17, 2004

(54) PORTABLE IMAGE ANALYSIS SYSTEM

(75) Inventors: Yair Kipman, Waban, MA (US); David Wolin, Arlington, MA (US); Katherine Johnson, Nashua, NH (US)

(73) Assignee: ImageXpert, Inc., Nashua, NH (US)

( * ) Notice: Subject to any disclaimer, the term of this patent is extended or adjusted under 35 U.S.C. 154(b) by 0 days.

(21) Appl. No.: 09/523,353

(22) Filed: Mar. 10, 2000

(51) Int. Cl.[7] .............................. G06K 9/20; G06K 9/22; H04N 1/24
(52) U.S. Cl. ..................... 382/313; 382/312; 358/473
(58) Field of Search ................................ 382/312–314, 382/315, 307, 309; 358/473, 474; 250/233, 334; 235/462.12

(56) References Cited

U.S. PATENT DOCUMENTS

| | | | | |
|---|---|---|---|---|
| 3,783,295 A | * | 1/1974 | Casler | 382/321 |
| 3,973,124 A | * | 8/1976 | Astheimer | 250/334 |
| 3,990,044 A | * | 11/1976 | Fahey et al. | 382/258 |
| 4,158,194 A | * | 6/1979 | McWaters et al. | 382/313 |
| 4,724,330 A | * | 2/1988 | Tuhro | 356/614 |
| 5,182,450 A | * | 1/1993 | Pan | 250/234 |
| 5,294,783 A | * | 3/1994 | Hammond et al. | 235/462.16 |
| 5,301,243 A | * | 4/1994 | Olschafskie et al. | 382/314 |
| 5,647,027 A | * | 7/1997 | Burges et al. | 382/275 |
| 5,923,444 A | * | 7/1999 | Bohn | 358/473 |
| 6,089,108 A | * | 7/2000 | Lucas | 73/865.8 |

* cited by examiner

Primary Examiner—Leo Boudreau
Assistant Examiner—Duy M. Dang
(74) Attorney, Agent, or Firm—Iandiorio & Teska

(57) ABSTRACT

A portable image analysis system including a hand held head assembly with an imaging window in the bottom of a housing, at least one light source in the housing directed at the imaging window, and an imaging device in the housing optically coupled to the imaging window. A computer, coupled to the hand held head assembly includes an imaging quality analysis program and a monitor for displaying images in the imaging window of the housing captured by the imaging device of the hand held head assembly for performing in situ image quality measurements.

24 Claims, 4 Drawing Sheets

PORTABLE IMAGE ANALYSIS SYSTEM

FIELD OF THE INVENTION

This invention relates to a portable image analysis system whereby documents and even raw paper can be inspected in situ.

BACKGROUND OF THE INVENTION

Raw paper is inspected and printers are tested, after printing a sample document, by stationary, fairly large image quality measurement systems which typically include a vibration isolation table, an X-Y translation stage, multiple cameras and illumination sources, and a computer operating a program like ImageXpert™ available from KDY, Inc., Nashua, N.H.

There is often a need, however, to spot check or inspect raw paper as it is manufactured and also a need to spot check or inspect one or more printers as they are in the process of printing sample documents.

Since traditional stationary image quality measurement systems are quite expensive and bulky, they are typically positioned in the factory in a specific test area or bay and thus they cannot easily be brought out onto the factory floor. Therefore, quality assurance personnel must transport samples to the test area, a process which increases the likelihood that samples will be damaged or lost in transit. Moreover, there is a time delay between sample collection and analysis which can adversely affect the inspection processes.

Currently, there is no known hand held camera based system for inspecting raw paper as it exits a particular paper making machine or for inspecting sample or test documents as they are printed by a new printer.

SUMMARY OF THE INVENTION

It is therefore an object of this invention to provide a portable image analysis system.

It is a further object of this invention to provide such a portable image analysis system which can be easily brought or carried onto the factory floor and used in situ to inspect raw paper, documents, and other surfaces.

It is a further object of this invention to provide such a portable imaging analysis system which is fairly inexpensive, reliable, and simple in design and construction.

This invention results from the realization that the features of documents, blank paper, and other surfaces can be spot checked and inspected in situ by (a) the combination of a lap top computer running an image quality analysis program coupled to a head assembly about the size of a computer mouse which includes a CCD camera, an imaging window, a number of LED light sources aimed at the window, and a diametrically opposed viewing window which allows the operator to correctly and precisely position the head assembly over the surface, (b) by the addition of a switching circuit for strobing the LED light sources at different frequencies depending on the reflectivity of the surface to eliminate the need for a mechanical aperture, and (c) by the addition of an integral calibration target which is disposed on the bottom of the head assembly and which can be slid out over the imaging window to calibrate the system.

This invention features a portable image analysis system including a hand held head assembly and a computer coupled to the head assembly. The head assembly has a housing, an imaging window in the bottom of the housing, at least one light source such as an LED in the housing directed at the imaging window, and an imaging device such as a CCD in the housing optically coupled to the imaging window. The computer typically includes an imaging quality analysis program and a monitor for displaying images in the imaging window of the housing captured by the imaging device of the hand held head assembly for performing in situ image quality measurements.

The housing preferably also includes a viewing window in the top thereof diametrically opposed from the imaging window, the viewing window optically coupled to the imaging window to allow an operator to correctly position the imaging window of the hand held head assembly over an area of interest. There is typically a beam splitter in the optical path between the imaging window and the viewing window, a lens responsive to the beam splitter, a mirror positioned to direct light from the lens onto the CCD, and a fixed iris or aperture device positioned between the lens and the mirror.

There are typically a plurality (e.g., four) LED light sources all directed at an angle with respect to the imaging window. Further included are means for strobing the light sources and means for adjusting the strobing frequency of the light sources to regulate the amount of light directed through the imaging window. Also included is a calibration target and means, such as a sleeve in the bottom of the housing proximate the imaging window, for removably positioning the calibration target under the imaging window for calibrating the system.

This invention also features a hand held assembly for a portable imaging system, the hand held assembly comprising a housing, an imaging window in the bottom of the housing, at least one light source in the housing directed at the imaging window, an imaging device in the housing for capturing an image of an object (e.g., a sample document) placed under the imaging window, and a switching circuit in the housing for adjusting strobing frequency of the at least one light source, the switching circuit including a processor responsive to a varying resistance switch input.

BRIEF DESCRIPTION OF THE DRAWINGS

Other objects, features and advantages will occur to those skilled in the art from the following description of a preferred embodiment and the accompanying drawings, in which.

Figure 1:
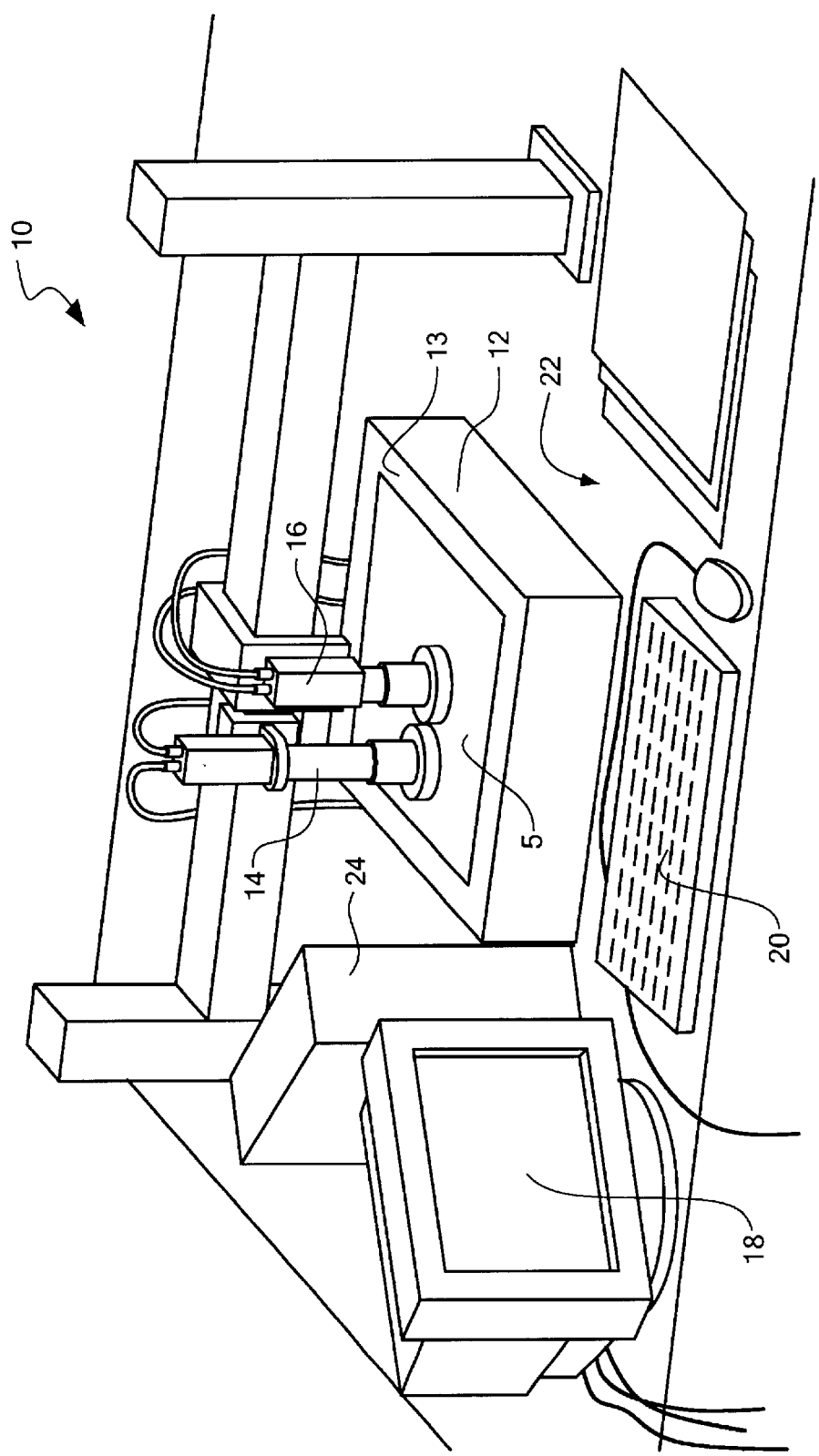
FIG. 1 is a schematic view of a typical prior art stationary image quality measurement system.

Fixed in place, fairly large, and usually quite expensive prior art image quality measurement system 10, FIG. 1 includes X-Y translation stage 12 disposed on vibration isolation table 22. A sample document 5 to be inspected for, inter alia, dot and line quality or a blank sheet to be inspected for dirt or aberrations is placed on surface 13 of translation stage 12 and cameras 14 and 16 connected to computer 24, which runs an image quality analysis program, in combination provide on display 18 a highly magnified image where even individual dots can be inspected automatically for uniformity and the like. Computer 24 and the image quality analysis program also operate translation stage 12 to move sample 5 under cameras 14 and 16 until the complete sample has been inspected and the results then displayed on monitor 18 and/or stored in a file associated with a particular sample which is traceable, for example, to a particular printer.

Such automatic image quality measuring systems are known in the art and include the ImageXpert™ hardware and software components available from KDY, Inc., Nashua, N.H.

As delineated in the Background of the Invention section above, however, there are times when quality assurance personnel would rather or in addition conduct tests or measurements at locations remote from the test area where stationary image quality measurement system 10, FIG. 1 is located. For example, a quality assurance inspector may wish to inspect a sample right after it exits a newly manufactured printer or inspect a sheet of raw paper as it exits a particular machine in a paper mill.

Figure 2:
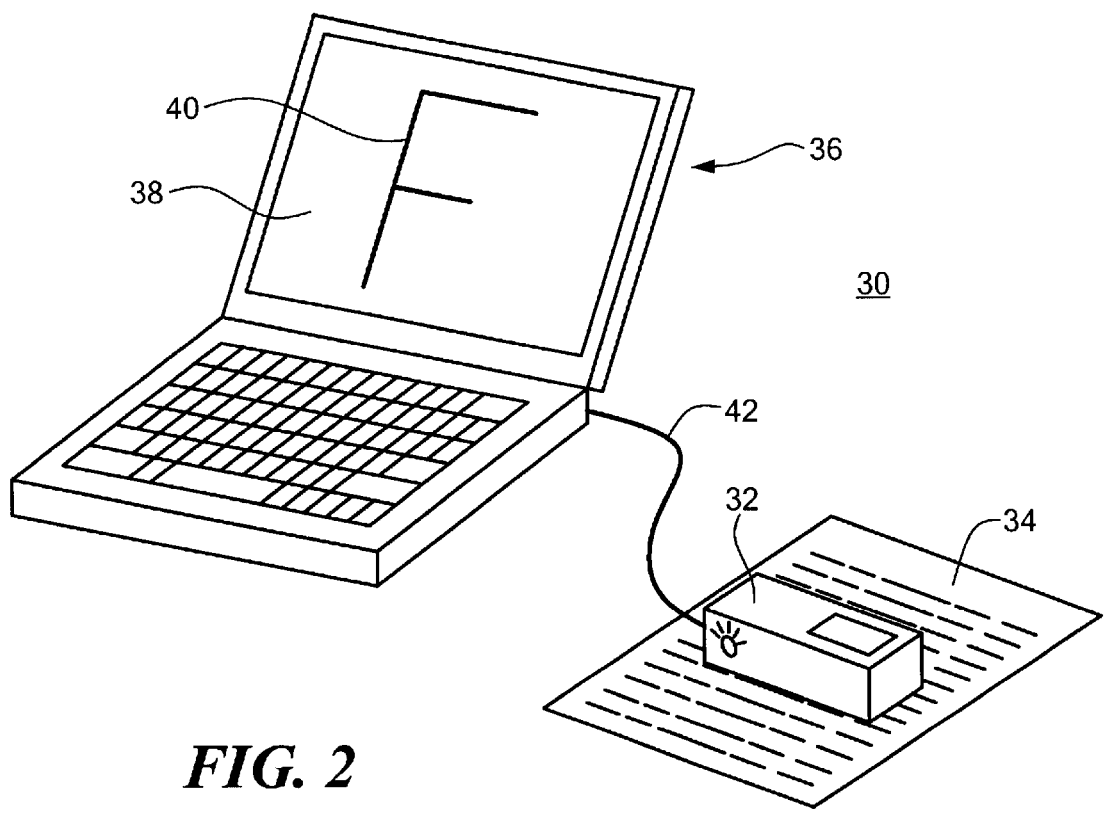
FIG. 2 is a schematic view of the portable image analysis system of the subject invention.

Thus, the present invention features portable image analysis system 30, FIG. 2. System 30 includes two primary components: hand held head assembly 32 which can be placed on sample 34 and computer 36, preferably a lap top computer with built-in monitor 38 for displaying a highly magnified image 40 captured by hand held head assembly 32. Lap top computer 36 is configured to run an image quality analysis program such as the ImageXpert™ software referred to supra.

Laptop computer 36 is coupled to hand held assembly 32 via cable 42 but alternative techniques exist including RF and infrared transmission hardware and software links in which case computer 36 need not necessarily be a laptop computer.

In the preferred embodiment, however, computer 36 is positioned close to sample 34 so quality assurance personnel can view image 40 in real time as head assembly 32 is moved over sample 34 and so the image quality assurance program operating on computer 36 can immediately provide the inspector with the desired test results.

Figure 3:
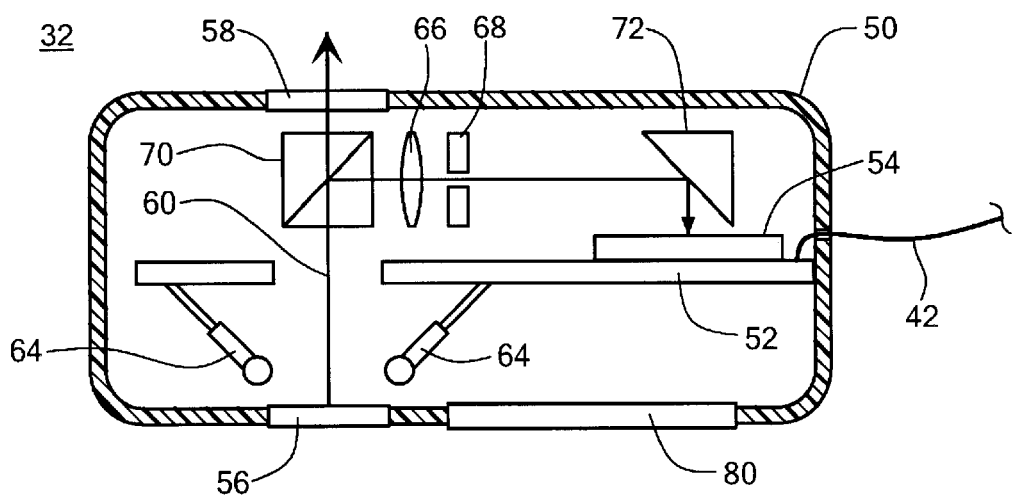
FIG. 3 is a side sectional view of the hand held head assembly of the portable image analysis system shown in FIG. 2.

The primary components of hand held head assembly 32 are shown in more detail in FIG. 3. Plastic housing 50 is a 4" long, 2" wide and 1.5" high computer mouse-like device and encloses circuit board 52 on which is disposed an imaging device such as CCD 54 and a switching circuit discussed infra. Also in housing 50 are two diametrically opposed windows 56 and 58. Imaging window 56 is in the bottom of housing 50 and viewing window 58 is in the top of housing 50. A set of four to six LED light sources 64 are arranged in a circle and directed at a 45 degree angle to direct light through imaging window 56 to strike a sample to be inspected. Reflected light as shown by arrow 60 travels through a hole in circuit board 52 and then passes through a viewing window 58. The reflected light is also directed through lens 66 and fixed aperture 68 by beam splitter 70. Thereafter, the reflected light strikes right angle mirror 72 and impinges on CCD 54 which captures an image of everything under imaging window 56. CCD image data is then transferred to computer 36 via cable 42.

Without viewing window 58, FIG. 2 it would be difficult for the operator to correctly position imaging window 56 over a specific feature of a sample to be imaged given the fact that the image on monitor 38, FIG. 2 is highly magnified. In FIG. 2, a complete letter is shown but often a single pixel or a short line segment of a letter or a feature of a letter is displayed. Thus, the combination of viewing window 58 in the top of housing 50 and diametrically opposed imaging window 56, FIG. 3 allows the operator to see the exact image captured by imaging window 56 and hence displayed on the computer monitor by virtue of CCD 54. Imaging window 56 and viewing window 58 are typically 13 mm square pieces of glass. Lens 66 is 10 mm in diameter and has a focal length of 20 mm. Aperture 68 defines a fixed opening of 6 mm.

Another feature of head assembly 32 is integral calibration target 80 disposed on the bottom of housing 50 such that it can be slid into position over imaging window 56 to calibrate, in connection with software running on computer 36, FIG. 1, head assembly 32 and all the optical components associated with it. Calibration target 80 is typically a thin 1 cm by 1 cm ceramic card with a number of different size pixels thereon. In one embodiment, the means for removably positioning calibration target 80, FIG. 4 under imaging window 56 is sleeve 84 recessed in the bottom of housing 50.

Still another feature of the subject invention is the ability to strobe LED light sources 64, FIG. 3 individually or as a set at different frequencies to account for the different reflectivity of sample documents.

Figure 5:
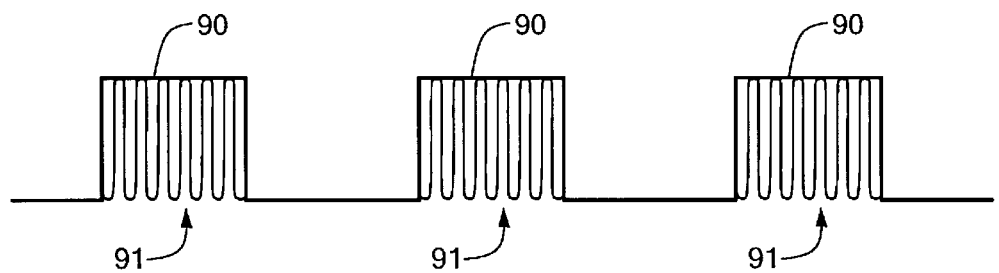
FIG. 5 is a waveform depicting the frame rate of the CCD camera of the subject invention and the associated LED strobe frequency for a white or highly reflective surface.
Figure 6:
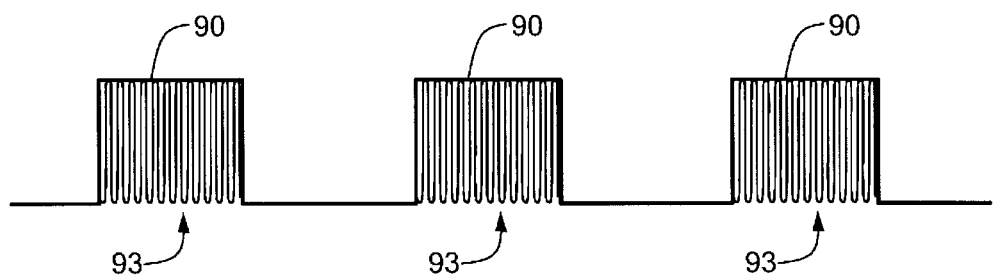
FIG. 6 is a figure similar to FIG. 5 except that now the LED strobing frequency is much higher when the surface to be inspected is dark or gray.
Figure 7:
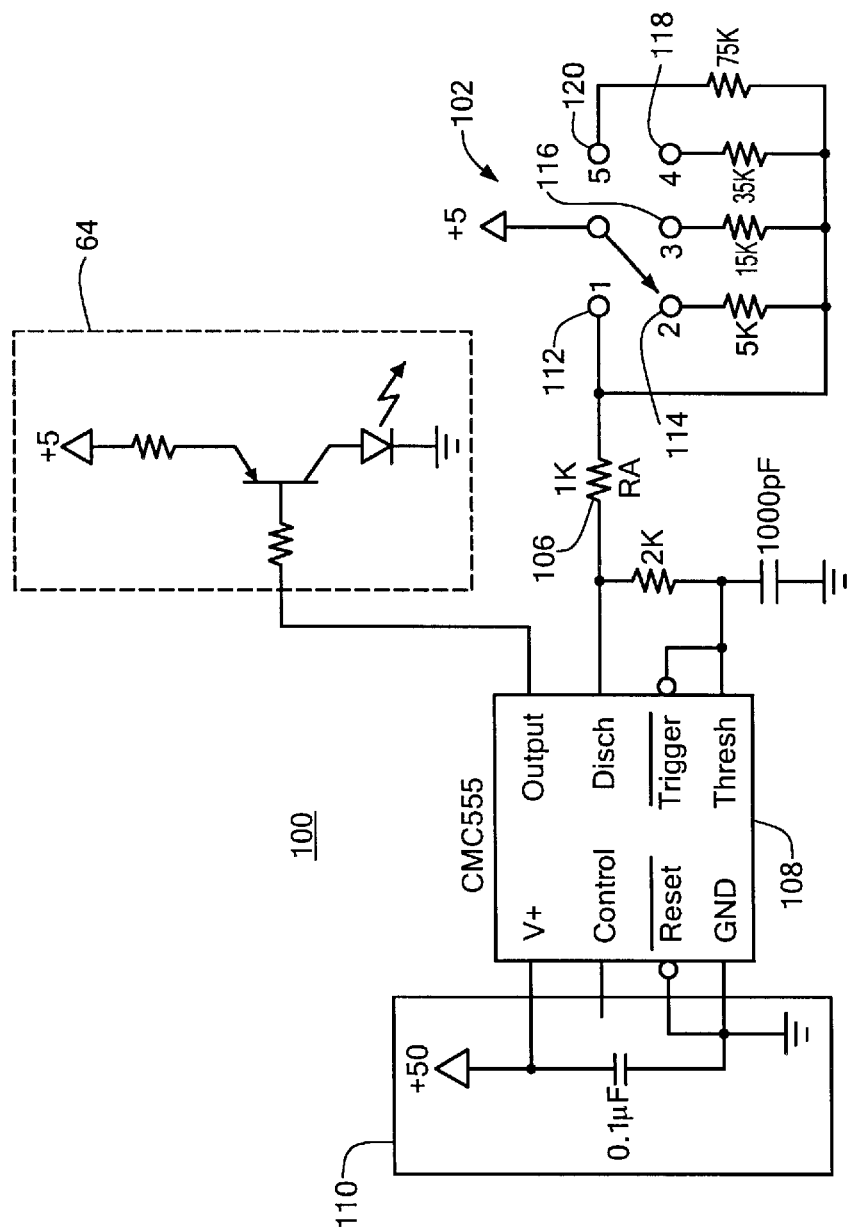
FIG. 7 is a schematic wiring diagram of the switching circuit which operates the LEDs to strobe at different frequencies as depicted in FIGS. 5 and 6.

As shown in FIGS. 5–6 where rises 90 depict the frame rate of the CCD camera (e.g., 30 frames per second), LEDs 64, FIG. 3 can be made to pulse 5 to 10 times per frame as shown at 91 when a white or highly reflective surface is being inspected (FIG. 5), or to pulse hundreds of times per frame as shown at 93 when a dark or gray sample is being inspected (FIG. 7). Thus, in this invention, there are means for strobing LED light sources 64, FIG. 3 at different frequencies to regulate the amount of light directed through imaging window 56.

This feature of the invention eliminates the need for a mechanical aperture and thus aperture 68 is fixed as described above. This LED strobing feature also eliminates the need to change the optics and/or programming of the system based on the light level and results in a more stable, more reliable, and less expensive camera system with less spherical aberration.

In the preferred embodiment, this means for strobing LED light sources 64 includes switching circuit 100, FIG. 7 on circuit board 52, FIG. 3.

Switching circuit 100 includes mechanical switch input 102 controlled by knob 104 on head assembly 32, FIG. 2. Knob 104 allows the user to manually chose between settings that correspond to f-stop-like changes in illumination. Each turn of the knob increases or decreases the amount of light for a given frame by a power of 2. Thus switch input 102 is, in the preferred embodiment, the means for adjusting the strobing frequency of the LEDs. Switch input 102 is connected in series with 1 KΩ resistor 106 as an input to the Disch port of CMC 555 microprocessor 108 powered by +5V input 110. The output port of processor 108 is connected to LED 64 as shown and in the preferred embodiment, to four LEDs. At position 1 (112) the total resistance is 1 KΩ which corresponds to a duty cycle of 40% and a strobing frequency of 288 KHz. At position 2 (114), the total resistance is 6 KΩ corresponding to a duty cycle of 20% and a strobing frequency of 144 KHz. At position 3 (116), the total resistance is 16 KΩ corresponding to a duty cycle of 10% and a strobing frequency of 72 KHz. At position 4 (118), the total resistance is 36 KΩ corresponding to a duty cycle of 5% and a strobing frequency of 36 KHz. At position 5 (120), the total resistance is 76 KΩ corresponding to a duty cycle of 2.5% and a strobing frequency of 18 KHz. Since no mechanical iris is included in the design of head assembly 32, FIG. 3, this novel approach was developed in order to mimic the f-stop illumination control of a traditional camera system. The solution is to operate the LED sources 64 at different frequencies. By controlling the number of illumination cycles per video frame, the illumination level for the frame can be controlled. Since the video frame rate is constant (30 frames per second) the system was designed to vary the number of illumination cycles. Thus, control circuit 100 is provided that allows the user to manually choose between 10 settings that correspond to f-stop-like changes in illumination. Each step in the control increases or decreases the amount of light for a given frame by a power of 2.

Figure 4:
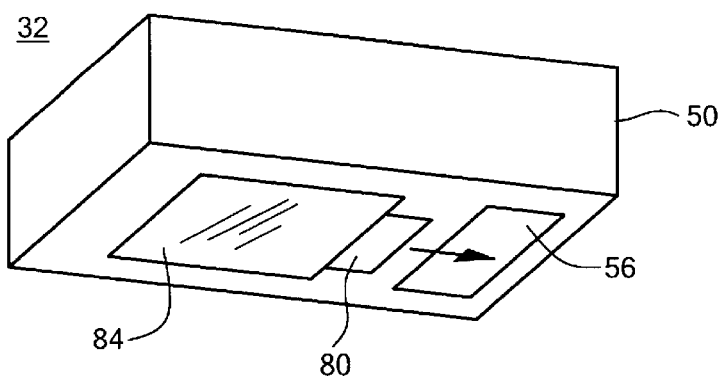
FIG. 4 is a schematic bottom view of the hand held head assembly shown in FIG. 3.

Thus, system 30, FIG. 2 and in particular the invention of hand held head assembly 32, FIGS. 3–4 allows quality assurance personnel to spot check in situ the features of documents, blank paper, and other surfaces. Imaging window 56, FIG. 3 and opposing viewing window 58 allows the operator to correctly and precisely position hand held head assembly 32 over the sample. Switching circuit 100, FIG. 7 strobes the LED light sources 64 at different frequencies depending on the reflectivity of the surface to eliminate the need for a mechanical aperture. Integral calibration target 80 disposed on the bottom of head assembly 32 can be slid out over imaging window 56 to calibrate the head assembly. Thus, portable image analysis system 30, FIG. 2 can conveniently be brought or carried onto the factory floor and used in situ to inspect raw paper, documents, and other surfaces. System 30 is also fairly inexpensive, reliable, and simple in design and construction.

Although specific features of the invention are shown in some drawings and not in others, this is for convenience only as each feature may be combined with any or all of the other features in accordance with the invention. Moreover, other embodiments will occur to those skilled in the art and are within the following claims. Also, the words "including", "comprising", "having", and "with" as used herein are to be interpreted broadly and comprehensively and are not limited to a particular physical interconnection. Finally, any embodiments disclosed in the subject application are not to be taken as the only possible embodiments.

What is claimed is:

1. A portable image analysis system comprising:
a hand held head assembly including:
a housing,
an imaging window in the bottom of the housing,
at least one light source, and
an imaging device in the housing optically coupled to the imaging window; and
a computer, coupled to the hand held assembly, the computer including:
an imaging quality analysis program, and
a monitor for displaying images in the imaging window of the housing captured by the imaging device of the hand held head assembly for performing in situ image quality measurements;
means for strobing the at least one light source; and
means for adjusting the strobing frequency of the at least one light source to regulate the amount of light directed through the imaging window.

2. The portable image analysis system of claim 1 in which the housing further includes a viewing window in the top thereof, the viewing window optically coupled to the imaging window to allow an operator to correctly position the imaging window of the hand held head assembly over an area of interest.

3. The portable image analysis system of claim 2 in which the viewing window is diametrically opposed from the imaging window.

4. The portable image analysis system of claim 3 in which the housing includes a beam splitter in the optical path between the imaging window and the viewing window.

5. The portable image analysis system of claim 4 in which the imaging device includes a CCD and the housing includes a lens responsive to the beam splitter, a mirror positioned to direct light from the lens onto the CCD, and an aperture device positioned between the lens and the mirror.

6. The portable image analysis system of claim 5 in which the aperture device defines a fixed aperture.

7. The portable image analysis system of claim 1 in which the at least one light source is an LED light source in the housing directed at the imaging window.

8. The portable image analysis system of claim 7 in which there are a plurality of LED light sources.

9. The portable image analysis system of claim 8 in which the LED light source are directed at an angle with respect to the imaging window.

10. The portable image analysis system of claim 1 further including a calibration target and means for removably positioning the calibration target under the imaging window for calibrating the system.

11. The portable image analysis system of claim 10 in which said means includes a sleeve in the bottom of the housing proximate the imaging window.

12. A hand held head assembly for a portable imaging system, the hand held head assembly comprising:
a housing;
an imaging window in the bottom of the housing;
a plurality of LED light sources in the housing directed at the imaging window;
a CCD device disposed on a circuit board in the housing;
a viewing window in the top of the housing diametrically opposed from the imaging window;
a beam splitter disposed in the housing to direct light from the imaging window to both the viewing window and the CCD device;
means for strobing at least one of the light sources; and
means for adjusting the strobing frequency of the at least one light source to regulate the amount of light directed through the imaging window.

13. The hand held head assembly of claim 12 further including a lens, a fixed aperture, and a mirror disposed between the beam splitter and the CCD device.

14. The hand held head assembly of claim 12 in which the circuit board further include a switching circuit for strobing the plurality of LED light sources collectively at different frequencies.

15. The hand held head assembly of claim 12 further including an integral calibration target disposed on the bottom of the housing proximate the imaging window.

16. A hand held head assembly for a portable imaging system, the hand held head assembly comprising:
a housing;
an imaging window in the bottom of the housing;
a plurality of LED light sources in the housing directed at the imaging window;

a CCD device disposed on a circuit board in the housing;

a switching circuit on the circuit board for strobing the plurality of LED light sources collectively at different frequencies;

means for strobing at least one of the light sources; and means for adjusting the strobing frequency of the at least one light source to regulate the amount of light directed through the imaging window.

17. The hand held head assembly of claim 16 further including a viewing window in the top of the housing diametrically opposed from the imaging window and a beam splitter disposed in the housing to direct light from the imaging window to both the viewing window and towards the CCD device.

18. The hand held head assembly of claim 17 further including a lens, a fixed aperture, and a mirror disposed between the beam splitter and the CCD device.

19. A hand held head assembly for a portable imaging system, the hand head assembly comprising:

a housing;

an imaging window in the bottom of the housing;

at least one light source in the housing directed at the imaging window;

an imaging device disposed on a circuit board in the housing; and a calibration target disposed on the bottom of the housing proximate the imaging window for calibrating the head assembly;

means for strobing the at least one light source; and means for adjusting the strobing frequency of the at least one light source to regulate the amount of light directed through the imaging window.

20. The hand held assembly of claim 19 further including a viewing window in the top of the housing diametrically opposed from the imaging window and a beam splitter disposed in the housing to direct light from the imaging window to both the viewing window and towards the imaging device.

21. The hand held head assembly of claim 20 further including a lens, a fixed aperture, and a mirror disposed between the beam splitter and the imaging device.

22. The hand held head assembly of claim 19 in which the circuit board further includes a switching circuit for strobing the at least one light source at different frequencies.

23. A hand held head assembly for a portable imaging system, the hand held assembly comprising:

a housing;

an imaging window in the bottom of the housing;

at least one light source;

an imaging device in the housing for capturing an image of an object placed under the imaging window; and a switching circuit in the housing for adjusting strobing frequency of the at least one light source, the switching circuit including a processor responsive to a varying resistance switch input.

24. A portable image analysis system comprising:

a hand held head assembly including:
 a housing,
 an imaging window in the bottom of the housing,
 at least one light source, and
 an imaging device in the housing optically coupled to the imaging window;

a computer, coupled to the hand held assembly, the computer including:
 an imaging quality analysis program, and
 a monitor for displaying images in the imaging window of the housing captured by the imaging device of the hand held head assembly for performing in situ image quality measurements;

means for strobing the at least one light source; and means for adjusting the strobing frequency of the at least one light source to regulate the amount of light directed through the imaging window.

* * * * *